(12) United States Patent
Noble

(10) Patent No.: US 9,198,903 B2
(45) Date of Patent: Dec. 1, 2015

(54) METHOD OF TREATING OR PREVENTING THROMBOSIS IN A PATIENT WITH 5-HT2A RECEPTOR ANTAGONIST THROMBOSERIN

(75) Inventor: Mark Ian Munro Noble, Angus (GB)

(73) Assignee: Thromboserin Limited, West Sussex (GB)

( * ) Notice: Subject to any disclaimer, the term of this patent is extended or adjusted under 35 U.S.C. 154(b) by 849 days.

(21) Appl. No.: 12/518,270

(22) PCT Filed: Feb. 28, 2008

(86) PCT No.: PCT/GB2008/000689
§ 371 (c)(1),
(2), (4) Date: Jun. 8, 2009

(87) PCT Pub. No.: WO2008/104789
PCT Pub. Date: Sep. 4, 2008

(65) Prior Publication Data
US 2010/0093791 A1    Apr. 15, 2010

Related U.S. Application Data

(60) Provisional application No. 60/891,971, filed on Feb. 28, 2007.

(51) Int. Cl.
*A61K 31/4704* (2006.01)
*A61K 38/48* (2006.01)
*A61K 31/47* (2006.01)
(Continued)

(52) U.S. Cl.
CPC .................. *A61K 31/47* (2013.01); *A61K 31/18* (2013.01); *A61K 31/517* (2013.01); *A61K 31/538* (2013.01); *A61K 45/06* (2013.01)

(58) Field of Classification Search
CPC ..... A61K 31/47; A61K 31/18; A61K 31/517; A61K 31/538; A61K 45/06; A61K 31/00; A61K 31/48; A61K 31/353; A61K 31/138
USPC ....................................................... 514/312
See application file for complete search history.

(56) References Cited

U.S. PATENT DOCUMENTS

| 4,435,405 A | 3/1984 | Blackburn et al. |
| 7,091,181 B2 * | 8/2006 | Demopulos et al. ........... 514/9.7 |
| 2005/0014757 A1 | 1/2005 | Andersson et al. |

FOREIGN PATENT DOCUMENTS

| EP | 0066993 A1 | 12/1982 |
| WO | 2008104789 A1 | 9/2008 |

OTHER PUBLICATIONS

Millson et al. The effects of a selective 5-HT 2 receptor antagonist (ICI 170,809) on platelet aggregation and pupillary responses in healthy volunteers, Br. J. clin. Pharmac. (1992), 33, 281-288.*

(Continued)

*Primary Examiner* — Savitha Rao
(74) *Attorney, Agent, or Firm* — Rodney B. Carroll; Conley Rose, P.C.

(57) ABSTRACT

There is provided the use of a 5-$HT_{2A}$ receptor antagonist to treat or prevent thrombosis, particularly arterial thrombosis, in a human or animal patient. The patient is suitably one who is at risk of bleeding, particularly those about to undergo, or those undergoing, surgery. A preferred 5-$HT_{2A}$ antagonist is thromboserin.

25 Claims, 1 Drawing Sheet

(51) Int. Cl.
  A61K 31/538    (2006.01)
  A61K 31/18     (2006.01)
  A61K 45/06     (2006.01)
  A61K 31/517    (2006.01)

(56) References Cited

OTHER PUBLICATIONS

Haulon et al. (Peripheral arterial revascularization: which antithrombotic agents?, Arch Mal Coeur Vaiss, Nov. 2001; 94(11 Suppl): 1278-84.*
Kihara et al. Antithrombotic activity of AT-1015, a potent 5-HT 2A receptor antagonist, in rat arterial thromboisis model and its effect on bleeding time, European Journal of Pharmacology 433 (2001) 157-162.*
Maxwell. C., Lower Gastro Intestinal Bleeding in the Elderly Sep. 5, 2008/vol. 15—Issue 4—Apr. 2007.*
Belcher et al. (Cardiovascular and Haematological Disorders-drug targets, Mar. 2006, pp. 43-55.*
Ando et al. (Remington pharmaceutical science, 2000, 20th Edition, pp. 704-711).*
McAullife et al. (British Journal of pharmacology (1994), 112, pp. 272-276.*
Antman, Elliott M., "The re-emergence of anticoagulation in coronary disease," European Heart Journal Supplements, 2004, vol. 6, Supplement B, pp. B2-B8, European Society of Cardiology, Elsevier Ltd.
Ashton, Juliet H., et al., "Serotonin as a mediator of cyclic flow variations in stenosed canine coronary arteries," Circulation, 1986, vol. 73, No. 3, pp. 572-578, American Heart Association, Dallas, Texas, US.
Ashton, Juliet H., et al., "Serotonin S2 and Thromboxane A2-Prostaglandin H2 Receptor Blockade Provide Protection Against Epinephrine-induced Cyclic Flow Variations in Severely Narrowed Canine Coronary Arteries," Journal of the American College of Cardiology, 1989, vol. 13, No. 3, pp. 755-763, American College of Cardiology.
Bakish, David, et al., "Effects of Selective Serotonin Reuptake Inhibitors on Platelet Serotonin Parameters in Major Depressive Disorder," Biol. Psychiatry, 1997, vol. 41, pp. 184-190, Society of Biological Psychiatry.
Belcher, Philip R., et al., "Antagonism of the platelet 5HT2 receptor in the presence of thrombolysis," International Journal of Cardiology, 1994, vol. 43, pp. 11-20, Elsevier Science Ireland Ltd.
Belcher, P. R., et al., "The Antiplatelet Drug Target in Atherosclerotic Diseases," Cardiovascular & Haematological Disorders—Drug Targets, 2006, vol. 6, No. 1, pp. 43-55. Bentham Science Publishers Ltd.
Belcher, Philip R., et al , "Dispersion of coronary artery thrombi by antagonism of platelet serotonin receptor in the dog," Cardiovascular Research, 1992, vol. 26, pp. 292-296.
Cerrito, F., et al., "5HT2-Receptors and Serotonin Release: Their Role in Human Platelet Aggregation," Life Sciences, 1993, vol. 53, pp. 209-215, Pergamon Press Ltd., US.
Drake-Holland, Angela J., "Modification of coronary artery disease using antithrombotic therapy," Journal of Cardiovascular Risk, 1995, vol. 2, pp. 229-233, Current Science.
Eckert, A., et al., "Elevated Intracellular Calcium Levels after 5-HT2 Receptor Stimulation in Platelets of Depressed Patients," Biol. Psychiatry, 1993, vol. 34, pp. 565-568, Society of Biological Psychiatry.
Foreign communication from the priority application—International Search Report and Written Opinion, PCT/GB2008/000689, May 19, 2008, 10 pages.
Foreign communication from the priority application—International Preliminary Report on Patentability, PCT/GB2008/000689, Feb. 20, 2009, 7 pages.
Francis, Gary S., et al., "Ask the Doctors," Heart Advisor, 2004, vol. 7 p. 8, Norwalk, CT, US.
Glassman, Alexander H., et al., "Sertraline Treatment of Major Depression in Patients with Acute MI or Unstable Angina," JAMA, 2002, vol. 288, No. 6, pp. 701-709, American Medical Association.
Goodman and Gilman's "The Pharmacological Basis of Therapeutics, Ninth Edition," Editors Martin J. Wonsiewicz and Peter McCurdy, 1996, Chapter 2, 15 pages, McGraw Hill Publishers, United States.
Grover, Gary J., et al., "Protective Effect of the Serotonin Receptor Antagonist Cinanserin in Two Canine Models of Pacing-Induced Myocardial Ischemia," Pharmacology, 1995, vol. 50, pp. 286-297, S. Karger AG, Basel.
Helmeste, Daiga M., et al., "Serotonin uptake inhibitors modulate intracellular Ca2+ mobilization in platelets," European Journal of Pharmacology, Molecular Pharmacology Section, vol. 288, 1095, pp. 373-377, Elsevier Science B.V.
Huo, Yuqing, et al., "Role of Platelets in the Development of Atheroscleros," Trends in Cardiovascular Medicine, 2004; vol. 14, pp. 18-22, Elsevier Inc.
Jackson, Shaun P., et al., "PI 3-kinase p110B: A new target for antithrombotic therapy," Nature Medicine, 2005, vol. 11, No. 5, pp. 507-514, Nature Publishing Group.
Kihara, Hideaki, et al., "Antithrombotic activity of AT-1015, a potent 5-HT2A receptor antagonist, in rat arterial thrombosis model and its effect of bleeding time," European Journal of Pharmacology, 2001, vol. 433, pp. 157-162, XP-002476706, Elsevier Science B.V.
Markovitz, Jerome H., et al., "Platelet Activation in Depression and Effects of Sertraline Treatment: An Open-Label Study," Am. J. Psychiatry, 2000, vol. 157, No. 6, pp. 1006-1008.
McAuliffe, S.J.G., et al., "Interaction between the effects of 5-hydroxytryptamine and adrenaline on the growth of platelet thrombi in the coronary artery of the anaesthetized dog," Br. J. Pharmacol., 1993, vol. 109, pp. 405-410, Macmillan Press Ltd.
Meier, Christoph R., et al., "Use of selective serotonin reuptake inhibitors and risk of developing first-time acute myocardial infarction," Br. J. Clin. Pharmacol., 2001, vol. 52, pp. 179-184, Blackwell Science Ltd.
Menys, Valentine C., "Collagen induced human platelet aggregation: serotonin receptor antagonism retards aggregate growth in vitro," Cardiovascular Research, 1993, vol. 27, pp. 1916-1919, XP 009098793.
Menys, V. C., et al., "Platelet 5-hydroxytryptamine is decreased in a preliminary group of depressed patients receiving the 5-hydroxytryptamine re-uptake inhibiting drug fluoxetine," Clinical Science, 1996, vol. 91, pp. 87-92, Great Britain.
Millson, D. S., et al., "The effects of a selective 5-HT2 receptor antagonist (ICI 170,809) on platelet aggregation and pupillary responses in healthy volunteers," Br. J. Clin. Pharmacology, 1992, vol. 33, pp. 281-286, XP-002476709.
Noble, Mark I. M., et al., "The involvement of serotonin in the formation of thrombi at critical coronary arterial stenoses in humans," Coronary Artery Disease, 1990, vol. 1, pp. 675-679, Current Science.
Noble, Mark I. M., et al., "Evidence for a Role of Serotonin in Initiation of Coronary Arterial Thrombosis in Dog and Man," Clin. Physiol. Biochem. 1990, vol. 8, Supplement 3, pp. 50-55, Karger AG, Basel.
Noble, M. I. M., et al., "The possible role of serotonin 5HT2 receptor antagonism in cardioprotection," Netherlands Journal of Medicine, 1992, vol. 41, pp. 183-189, Elsevier Science Publishers B.V.
Noble M. I. M., et al., "The role of serotonin 5HT2 receptor antagonism in the control of coronary artery disease," Quarterly Journal of Medicine, 1994, vol. 87. pp. 11-16, Oxford University Press.
Pandey, Ghanshyam N., et al., "Platelet Serotonin-2 Receptor Binding Sites in Depression and Suicide," Biol. Psychiatry, 1990, vol. 28. pp. 215-222. Society of Biological Psychiatry.
Rosel, P., et al., "Altered [3H]imipramine and 5-HT2 but not [3H]paroxetine binding sites in platelets from depressed patients," Journal of Affective Disorders, 1999, vol. 52, pp. 225-233, Elsevier Science B.V.
Serebruany, Victor L., et al., "Enhanced platelet/endothelial activation in depressed patients with acute coronary syndromes: evidence from recent clinical trials," Blood Coagulation and Fibrinolysis, 2003, vol. 14, pp. 563-567, Lippincott Williams and Wilkins.

(56) References Cited

OTHER PUBLICATIONS

Shaw, Linda A., et al., "Suppression of reperfusion-induced arrhythmias with combined administration of 5-HT2 and thromboxane A2 antagonists," British Journal of Pharmacology, 1996, vol. 117, pp. 817-822, Stockton Press.

Steinhubl, Steven R., et al., "Point-of-care Measured Platelet Inhibition Correlates With a Reduced Risk of an Adverse Cardiac Event After Percutaneous Coronary Intervention: Results of the GOLD (AU-Assessing Ultegra) Multicenter Study," Circulation, 2001, vol. 103, pp. 2572-2578, American Heart Association, Dallas, Texas, US.

Torr, Sheryl, et al., "Inhibition of Acute Platelet Thrombosis Formation in Stenosed Canine Coronary Arteries by Specific Serotonin 5HT2 Receptor Antagonist Ritanserin," Cardiovascular Research, 1990, vol. XXIV, No. 6, pp. 465-470, British Medical Association, London.

Vikenes, Kjell, et al., "Serotonin is Associated with Coronary Artery Disease and Cardiac Events," Circulation, 1999, vol. 100, pp. 483-489, American Heart Association, Dallas, Texas, US.

Vincentelli, Andre, et al., "Antithrombotic therapy in cardiac surgery," Canadian Journal of Anesthesia, 2006, vol. 53, No. 6 Supplement, pp. S89-S102, XP002476711.

Wallentin, L., "Oral direct thrombin inhibition for anticoagulation in coronary artery disease—focus on the ESTEEM trial," European Heart Journal Supplements, 2004, vol. 6, Supplement B, pp. B9-B14, European Society of Cardiology, Elsevier Ltd.

Wheeler, Guy L., "The Ultegra rapid platelet-function assay: comparison to standard platelet function assays in patients undergoing, percutaneous coronary intervention with abciximab therapy," American Heart Journal, 2002, vol. 143, No. 4, pp. 602-611, Mosby, Inc.

Yamada, Shinichiro, et al., "T102C polymorphism of the serotonin (5-HT) 2A receptor gene in patients with non-fatal acute myocardial infarction," Atherosclerosis, 2000, vol. 150, pp. 143-148, Elsevier Science Ireland Ltd.

Cohen, Hillel W., et al., "Excess Risk of Myocardial infarction in Patients Treated with Antidepressant Medications: Association with Use of Tricyclic Agents*," Am. J. Med., 2000, vol. 108, pp. 2-8, Excerpta Medica, Inc.

* cited by examiner

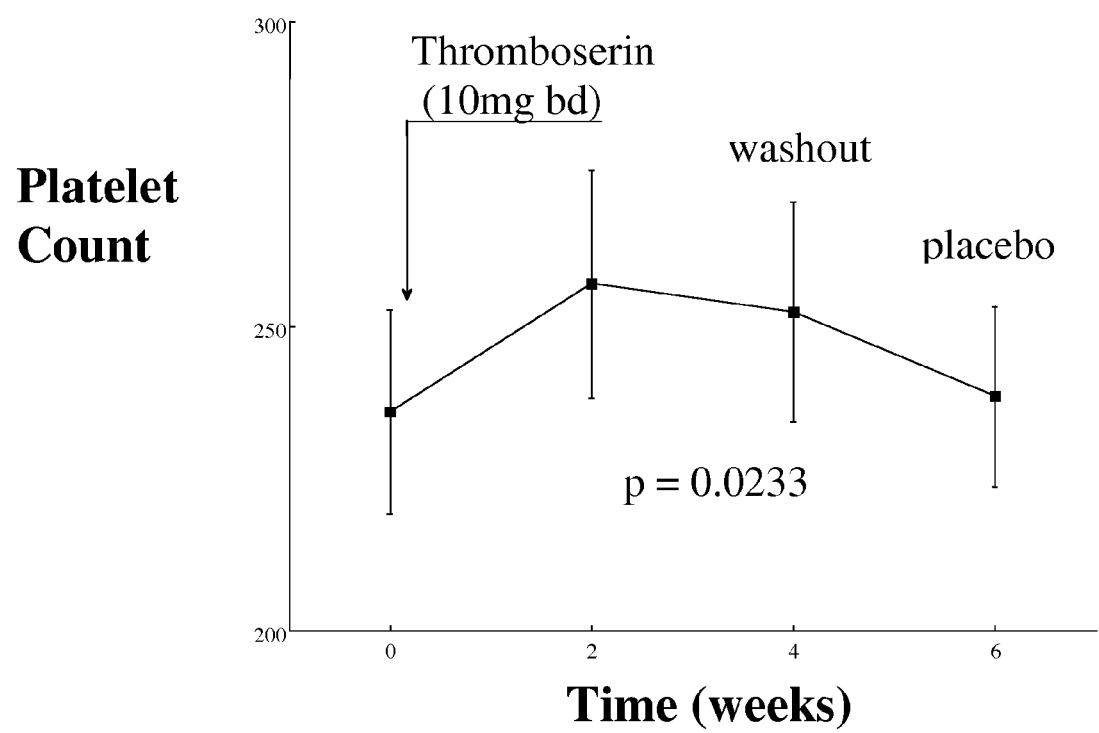

METHOD OF TREATING OR PREVENTING THROMBOSIS IN A PATIENT WITH 5-HT2A RECEPTOR ANTAGONIST THROMBOSERIN

CROSS-REFERENCE TO RELATED APPLICATIONS

This application is a filing under 35 U.S.C. 371 of International Application No. PCT/GB2008/000689 filed Feb. 28, 2008, entitled "Therapeutic Compositions," claiming priority of U.S. Patent Application No. 60/891,971 filed Feb. 28, 2007, which applications are incorporated by reference herein in their entirety.

FIELD OF THE INVENTION

The present invention relates generally to methods and materials for use in the treatment of arterial thrombosis e.g. atherosclerotic disease.

BACKGROUND OF THE INVENTION

A blood clot within an artery is known as an arterial thrombosis. Arterial thrombosis is responsible for heart attacks, strokes and peripheral vascular disease (thrombosis in leg arteries). Heart attacks and strokes are a major cause of death and serious illness. In the UK, 25 per cent of male deaths are due to a heart attack, while about 12 per cent of deaths are due to a stroke. Strokes are also the major cause of disability in the Western world.

Arterial thrombosis is primarily platelet-mediated, either due to increased shear or exposed collagen.

Anticoagulatants may be used for control of cardiovascular disease [16]. However there are two major problems with heparins and coumarin derivatives (like warfarin) which are that they cause bleeding and are most effective in fibrin-rich thrombosis, such as that seen in venous thrombosis and arterial fibrillation, but not in platelet-rich (arterial) thrombosis.

The same limitations affect pure thrombin inhibitors like ximelagatran [17].

In order to obtain favourable modification of platelet-induced arterial thrombosis in atherosclerotic disease (increasingly being called atherothrombosis), antiplatelet agents are used. The reversal of platelet activation in atherosclerosis has been shown to have a favorable outcome [2].

Aspirin has been the most widely used agent; it blocks the thromboxane pathway effectively. However due to certain limitations with aspirin, a newer drug, clopidogrel, is currently preferred. This antagonises the $P2Y_{12}$-receptor. Present therapies such as those discussed above may cause bleeding by interference with COX1, the $P2Y_{12}$ receptor or the platelet fibrinogen receptor complex, all of which can be associated with bleeding complications. There is also resistance in the population to certain of these therapies [139].

Thus it can be seen that methods and materials which could modulate platelet-induced arterial thrombosis without significant bleeding complications would represent a contribution to the art.

It has been claimed that blockade of the (P13K)p110β isoform of the GPIIb/IIIa adhesion bonds eliminates occlusive thrombus formation without prolonging bleeding time [152].

The use of the antiplatelet drug target in atherosclerotic diseases is discussed by Belcher, Drake-Holland, and Noble in Volume 6, Number 1, March 2006, pp. 43-55(13) (Bentham Science Publishers). The document is a general review of antiplatelet therapy based on the mechanisms of platelet rich arterial thrombosis.

SUMMARY OF THE INVENTION

Serotonin (5-hydroxytryptamine, 5HT) is present in high concentration in blood platelets. In contrast to the targets above serotonin does not influence formation of haemostatic layers (e.g. in wound healing) although it is implicated in shear-induced aggregation and thrombus propagation by positive feedback from the large amount of intraplatelet serotonin. However, surprisingly, to date serotonin antagonism has not progressed to clinical application. Platelets are the richest source of serotonin in the body outside the brain.

Platelets acquire serotonin from the plasma by means of the cell membrane serotonin uptake mechanism, and store the serotonin in dense granules Inhibition of this mechanism by serotonin reuptake inhibitors (SSRIs) causes depletion of platelet serotonin [82].

Upon platelet activation (especially with high shear) high concentrations of serotonin in the platelets are released from the dense granules [142], and act upon platelet serotonin $5HT_{2A}$ receptors to activate more platelets, thus constituting a positive feedback mechanism leading to thrombus growth. The serotonin theory [143-146] supposes that this serotonin mediation is essential for thrombotic occlusion of diseased coronary arteries, owing to the fact that such occlusions are abolished by antagonism of the platelet $5HT_{2A}$ receptor [95, 97] even when the major stimulus of adrenaline is applied [94] and also in the circumstances where thrombolysis has failed to clear a complete thrombotic occlusion [147].

Examination of patients undergoing angiography has showed that a high plasma serotonin level was significantly associated with coronary artery disease in patients younger than 70. In nearly four years of follow up high serotonin levels were also associated with cardiac events. This association persisted after adjustment for conventional risk factors [148]. There is some evidence for the T102C polymorphism of the $5HT_{2A}$ receptor gene as the cause of increased expression of $5HT_{2A}$ receptors; such increased expression is more prevalent in coronary thrombosis patients than in controls [149]. Platelets in patients with this gene polymorphism showed greater aggregatory responses to serotonin and adrenaline [150]. $5HT_{2A}$ antagonism was advocated in the treatment of coronary artery disease [151] in which some positive preliminary results were published [143].

Coincidentally, the frequent use of SSRIs to treat depression after acute coronary syndromes (because other antidepressants are cardiotoxic [153]) has led to the realisation that these drugs also reduce the consequences of platelet-rich thrombus growth [154-159], in spite of the fact that the activation of platelets by acute coronary syndromes is enhanced by depression In the case of SSRIs, the benefits arise from the fact that there is less serotonin in the platelets to be released upon activation [82], and thus there is less serotonin to activate other platelets through their $5HT_{2A}$ receptors. The findings of several investigators that there is increased binding of platelet $5HT_{2A}$ receptors as well as greater responsiveness of these receptors emphasises their importance [161] [162] [163].

The beneficial effects of serotonin antagonism in animal models of intracoronary thrombosis have been well shown [95,97,166,167], including as an adjunct to thrombolysis [147], and in 'demand-induced myocardial ischaemia' [168].

The effective serotonin receptor on platelets is the $5HT_{2A}$ receptor, which plays little, if any role in the central nervous system. Thus blocking the $5HT_{2A}$ receptor does not affect brain function.

Crucially, the present inventors have shown that $5HT_{2A}$ receptor antagonism does not cause excess bleeding.

Thus, in the light of this disclosure, it can be understood that selective serotonin $5HT_2$ antagonism can allow effective management of intravascular thrombosis without bleeding complications.

In its broadest aspect, the present invention provides the use of a $5\text{-}HT_{2A}$ receptor antagonist to treat or prevent thrombosis in a human or animal patient. Preferably, the thrombosis is arterial thrombosis.

Another aspect of the present invention provides the use of a $5\text{-}HT_{2A}$ receptor antagonist in the manufacture of a medicament to treat or prevent thrombosis.

Preferably, the patient is one who is at risk of bleeding. In particular, the invention is applicable to those who are about to undergo, or are undergoing, surgery.

Suitable $5\text{-}HT_{2A}$ receptor antagonists for use in the present invention comprise compounds of the formula I or a pharmaceutically acceptable salt thereof,

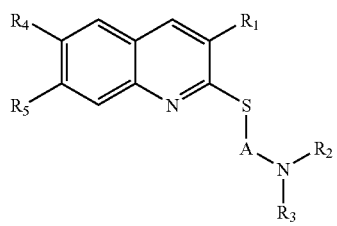

I wherein;

A stands for the radical —$(CH_2)_2$—, which may optionally be substituted by one or two (1-2C) alkyl radicals or it may be substituted by an alkylene radical so as to form, together with the residue of the —$(CH_2)_2$— radical, a cycloalkylene radical of not more than 6 carbon atoms;

$R^1$ stands for an n-, iso- or s-(3-4C) alkyl radical, or a cyclopropyl radical, or $R^1$ stands for a phenyl radical which may optionally be substituted with one or two substituents, in the latter case the same or different substituents, selected from halogen atoms and hydroxy, (1-4C) alkyl, (1-4C) alkoxy, (1-4C) alkylthio, (1-2C) perfluoro-alkyl, cyano, carboxy, (1-2C) alkylthio, (1-2C) alkoxy-carbonyl, carbamoyl, N-[(1-3C) alkyl carbamoyl and N,N-di-[(1-3C) alkyl]carbamoyl radicals, or $R^1$ stands for a heteroaryl radical of five or six ring atoms containing a single hetero-atom selected from oxygen, sulphur and nitrogen atoms or containing two hetero-atoms which are either a nitrogen atom and a sulphur atom or a nitrogen atom and an oxygen atom, which heteroaryl radical may optionally be substituted with a (1-3C) alkyl radical;

$R^2$ and $R^3$, which may be the same or different, stand for hydrogen or a methyl or ethyl radical, or $R^2$ stands for a dimethylene, trimethylene or tetramethylene radical which is linked to one or other of the carbon atoms forming the two-carbon-atom-backbone of the radical A so as to form, together with the adjacent nitrogen atom, a pyrrolidinyl or piperidyl radical; and One of $R^4$ and $R^5$ stands for hydrogen, and the other stands for hydrogen, a halogen atom, or a (1-3C)alkyl or (1-3C) alkoxy radical.

One preferred aspect of the present invention provides for the use of a $5\text{-}HT_{2A}$ receptor antagonist compound of formula II wherein "Me" stands for a Methyl group, or a pharmaceutically acceptable salt thereof, to treat or prevent thrombosis in a human or animal.

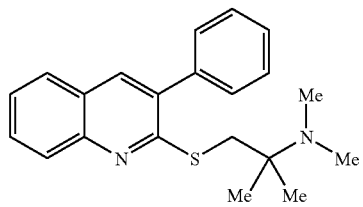

II

Accordingly, the invention provides a method of treatment or prophylaxis of thrombosis (for example arterial thrombosis) in a patient at risk of bleeding, which method comprises administering to the patient a therapeutically effective amount of an $5HT_{2A}$ antagonist.

In another aspect, the invention provides a method of inhibiting platelet aggregation leading to a thrombus in a patient (e.g. leading to propagated thrombus growth and\or occlusive arterial thrombus) while substantially not inhibiting platelet binding to the arterial cell wall, which method comprises administering to the patient a therapeutically effective amount of an $5HT_{2A}$ antagonist.

Such methods may be used for substantially inhibiting the potential for 'in vessel' blood clotting while substantially not inhibiting potential for 'bleed out' blood clotting after vessel puncture. This has the benefit of minimising the side effect of bleeding whilst on antithrombotic therapy.

Also provided is use of a $5HT_{2A}$ antagonist to inhibit platelet aggregation leading to a thrombus while substantially not inhibiting platelet binding to the arterial cell wall.

Such methods are particularly applicable for prophylaxis and would also allow cardioprotection of vascular patients undergoing surgical operations.

BRIEF DESCRIPTION OF THE DRAWINGS

Reference is made to the accompanying drawing, in which:
FIG. 1 is the effect on platelet count shown by repeated measured analysis of variance in the patients given Thromboserin first.

DETAILED DESCRIPTION OF THE INVENTION

Some aspects and embodiments of the present invention will now be described in more detail.
Arterial Thrombosis Treatment or prophylaxis of arterial thrombosis may be in a patient who is diagnosed with, or believed to be at risk of, such a thrombosis. By way of non-limiting example this may be in the context of or associated with cerebrovascular accident (e.g. ischaemic stroke), myocardial infarction (e.g. coronary thrombosis), thoracic outlet syndrome (may precipitate arterial thrombosis as well as venous). Other arterial thromboses may be associated with peripheral vascular disease.
Patient Groups Patients at risk of bleeding include (but are not limited to):
(i) Patients undergoing surgical operations or invasive instrumental procedures, particularly the elderly and those with concomitant chronic disease who frequently suffer arterial thrombotic occlusion before, during or after the intervention. Generally, an elderly patient is one who is over 50 years old, preferably someone around 60 years old or above.

(ii) Patients with a source of bleeding, e.g., from gastrointestinal, urinary tract or cerebral lesions, who are also at risk of thrombotic arterial disease.

(iii) Patients for whom present anti-thrombotic therapies are contra-indicated because of bleeding risk.

A preferred treatment is the pre-operative treatment of patients at high risk of cardiovascular complications following surgery.

Examples of surgical operations include, but are not limited to, peripheral angioplasty, coronary angioplasty and coronary artery bypass. Patients undergoing these procedures are preferred patient groups. A 5-HT$_{2A}$ receptor antagonist, particularly thromboserin, can be given either pre- or post operatively to these groups.

5HT$_{2A}$ Antagonists

The term "antagonist" as used herein, is used in its standard meaning to mean a chemical substance that opposed the physiological effects of another substance. In other words, an antagonist is a chemical substance that opposes the receptor-associated responses normally induced by another bioactive agent (in this case, serotonin release from platelets which would cause growth of arterial thrombus).

The 5HT$_{2A}$ antagonist may be non-specific, in the sense of inhibiting the effect of other 5HT receptors or 5HT more generally.

However, preferably the 5HT$_{2A}$ antagonist is specific, in the sense of not inhibiting the effect of other 5HT receptors or 5HT more generally.

The antagonists useful herein generally have an I$_{50}$ value from about 0.1 μg/kg to 100 mg/kg, wherein the inhibition being measured is the rate of growth of the thrombus and 'kg' represents the weight of the patient using I.V. administration of the compound.

EP 0066993 describes quinoline derivatives with the following formula:

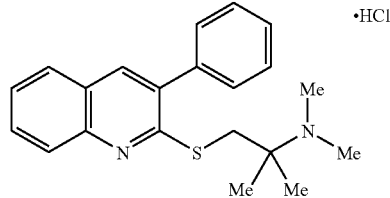

A stands for the radical —(CH$_2$)$_2$—, which may optionally be substituted by one or two (1-2C) alkyl radicals or it may be substituted by an alkylene radical so as to form, together with the residue of the —(CH$_2$)$_2$— radical, a cycloalkylene radical of not more than 6 carbon atoms;

R$^1$ stands for an n-, iso- or s-(3-4C) alkyl radical, or a cyclopropyl radical, or R$^1$ stands for a phenyl radical which may optionally be substituted with one or two substituents, in the latter case the same or different substituents, selected from halogen atoms and hydroxy, (1-4C) alkyl, (1-4C) alkoxy, (1-4C) alkylthio, (1-2C) perfluoro-alkyl, cyano, carboxy, (1-2C) alkylthio, (1-2C) alkoxy-carbonyl, carbamoyl, N-[(1-3C) alkyl carbamoyl and N,N-di-[(1-3C) alkyl]carbamoyl radicals, or R$^1$ stands for a heteroaryl radical of five or six ring atoms containing a single hetero-atom selected from oxygen, sulphur and nitrogen atoms or containing two hetero-atoms which are either a nitrogen atom and a sulphur atom or a nitrogen atom and an oxygen atom, which heteroaryl radical may optionally be substituted with a (1-3C) alkyl radical;

R$^2$ and R$^{3'}$ which may be the same or different, stand for hydrogen or a methyl or ethyl radical, or R$^2$ stands for a dimethylene, trimethylene or tetramethylene radical which is linked to one or other of the carbon atoms forming the two-carbon-atom-backbone of the radical A so as to form, together with the adjacent nitrogen atom, a pyrrolidinyl or piperidyl radical; and One of R$^4$ and R$^5$ stands for hydrogen, and the other stands for hydrogen, a halogen atom, or a (1-3C)alkyl or (1-3C) alkoxy radical;

and pharmaceutically acceptable acid-addition salts thereof.

EP 0066993 discusses the use of such compounds as 5-HT (serotonin) antagonists for platelet aggregation but did not propose their use to treat patients undergoing surgical procedures or having a high risk of bleeding.

Preferred 5HT$_{2A}$ antagonists for use in the present invention may be those described in EP 0066993.

A preferred 5HT$_{2A}$ antagonist is "Thromboserin" or other pharmaceutically acceptable acid-addition salt thereof. This is a pure 5HT$_{2A}$ antagonist without reported significant side effects and has the following formula.

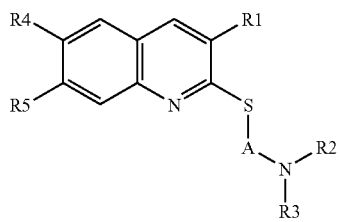

Thromboserin is described in the literature as ICI 170809 and its antiplatelet thrombus growth inhibition characterized in detail in "Interaction between the effect of 5-hydroxytryptamine and adrenaline on the growth of platelet thrombi in the coronary artery of the anaesthetised dog". McAuliffe S J G, Snow H M, Cox B, Smith C T T, Noble M I M. British Journal of Pharmacology 1993; 109:405-410. Once again this citation did not discuss its use to treat patients undergoing surgical procedures or having a high risk of bleeding.

Those skilled in the art will appreciate that other 5HT$_{2A}$ antagonists may also be used.

Sarpogrelate is a 5HT$_{2A}$ antagonist used in cardiovascular disease and there is considerable experiment evidence of its ability to modify the response to ischaemia [171].

Ketanserin was the first 5-HT$_{2A}$ receptor blocker but also had alpha-1 adrenergic antagonistic properties [169]. Unfortunately, ketanserin has pro-arrhythmic properties in the presence of hypokalaemia [170],which make it unsuitable for routine clinical use.

Anplag is a 5-HT$_{2A}$ antagonist with an indication for the prevention of recurrence of cerebral infarction in phase III development.

Combinations of Therapeutics

The treatments used herein may be used in combination with other treatments in the same patient—for example other atherothrombotic treatments selected from the list consisting of: aspirin, statins, β-blockers, ACE inhibitors, Angio II receptor antagonists, diuretics, nicorandil, nitrates, plus drugs used for the treatment of diabetes and arthritis. Use of a 5-HT$_{2A}$ antagonist in conjunction with any of these, in the patient groups described herein, forms one aspect of the present invention. Thromboserin is believed to have good compatibility with these agents.

Dosage of Therapeutics

Administration of compounds, compositions or medicaments as described herein is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

See also, Goodman and Gilman's, The Pharmacologic Basis of Therapeutics, 9th edition, 1996, chapter 2, E. M. Ross, Pharmacodynamics, Mechanisms of Drug Action and the Relationship Between Drug Concentration and Effect, which is incorporated by reference herein in its entirety.

Dosage for the compounds described herein may show therapeutic benefit at levels as low as 0.5 μg/kg (e.g. 35 μg in a 70 Kg man).

Preferred dosages may be in the range 0.005 μg-100 mg/kg at suitable intervals e.g. 1, 2, or 3 times per day orally.

Thus, for the treatment of platelet rich thrombosis when under high stimulation from adrenaline, between 0.01-100 mg e.g. between 0.1-20 mg e.g. between 1-20 mg e.g. between 3.5-15 mg about 10 mg twice or three times a day may be preferred (or double these for heavier patients over 100 kg).

Formulation and Administration of Therapeutics

Suitable compounds, such as those with a formula as shown above or their pharmaceutically acceptable salts, may be incorporated into compositions of this aspect of the present invention after further testing for toxicity.

The compositions may include, in addition to the above constituents, pharmaceutically-acceptable excipients, preserving agents, solubilizers, viscosity-increasing substances, stabilising agents, wetting agents, emulsifying agents, sweetening agents, colouring agents, flavouring agents, salts for varying the osmotic pressure, buffers, or coating agents. Such materials should be non-toxic and should not interfere with the efficacy of the active ingredient. The precise nature of the carrier or other material may depend on the route of administration. Examples of techniques and protocols can be found in "Remington's Pharmaceutical Sciences", 16$^{th}$ edition, Osol, A. (ed.), 1980.

Where the composition is formulated into a pharmaceutical composition, the administration thereof can be effected parentally such as orally, in the form of powders, tablets, coated tablets, dragees, hard and soft gelatine capsules, solutions, emulsions or suspensions, nasally (e.g. in the form of nasal sprays) or rectally (e.g. in the form of suppositories). However, the administration can also be effected parentally such as intramuscularly, intravenously, cutaneously, subcutaneously, or intraperitoneally (e.g. in the form of injection solutions).

Thus, for example, where the pharmaceutical composition is in the form of a tablet, it may include a solid carrier such as gelatine or an adjuvant. For the manufacture of tablets, coated tablets, dragees and hard gelatine capsules, the active compounds and their pharmaceutically acceptable acid addition salts can be processed with pharmaceutically inert, inorganic or organic excipients. Lactose, maize, starch or derivatives thereof, talc, stearic acid or its salts etc. can be used, for example, as such excipients for tablets, dragees and hard gelatine capsules. Suitable excipients for soft gelatine capsules are, for example, vegetable oils, waxes, fats, semi-solid and liquid polyols etc. Where the composition is in the form of a liquid pharmaceutical formulation, it will generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may also be included. Other suitable excipients for the manufacture of solutions and syrups are, for example, water, polyols, saccharose, invert sugar, glucose, trihalose, etc. Suitable excipients for injection solutions are, for example, water, alcohols, polyols, glycerol, vegetable oils, etc. For intravenous, cutaneous or subcutaneous injection, or intracatheter infusion into the brain, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, and Lactated Ringer's Injection. Preservatives, stabilisers, buffers and/or other additives may be included, as required.

Any sub-titles herein are included for convenience only, and are not to be construed as limiting the disclosure in any way.

The invention will now be further described with reference to the following non-limiting Figures and\or Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

EXAMPLES

Example 1

Normal Bleeding with Antiplatelet Therapy Using Serotonin 5HT2 Antagonism

Objective: To evaluate whether inhibition platelets can be accompanied by no increase in bleeding time, by means of serotonin 5HT$_{2A}$ receptor antagonism.

Study population: Patients with a history of intermittent claudication (IC) or coronary heart disease (CHD) recruited. There were 48 patients studied, all of whom were Caucasian, aged 69±6.6 years and of which 38 were male and 10 female. Patients with IC have clinical findings of peripheral vascular disease and an ABPI <0.9. Patients with CHD have chronic stable angina and angiographic evidence of coronary artery disease (stenosis of >70% in at least one major coronary artery).

Study design: Randomised controlled double blind crossover study: 2 weeks 5HT$_{2A}$ receptor antagonist (Thromboserin) (10 mg twice daily) or placebo, wash out period of 2 weeks and cross over to other arm for further two weeks. Side effects, and compliance documented in both groups.

Study duration: 12 months

Inclusion criteria: All patients on treatment with a statin and aspirin (≥75 mg daily) for a minimum of 6 weeks.

Exclusion criteria: Patients with IC who had rest pain or ulceration were excluded, as were patients who had symptoms suggestive of unstable CHD within the prior 12 weeks. Patients receiving treatment with clopidogrel, warfarin, nonsteroidal anti-inflammatory or serotonin reuptake inhibitor drugs were excluded, as were those with hepatic impairment or abnormal platelet count.

Blood sampling/Assays: Blood samples obtained at baseline, 2 weeks (the end of phase 1), 4 weeks (the end of phase 2), at 6 weeks (the end of phase 3) and 2 weeks after the completion of the study. The following assays were obtained.

Full blood count, urea, electrolytes, creatinine, liver function tests and glucose Blood levels of Thromboserin Bleeding time Surface expression of the platelet activation markers P-selectin and fibrinogen. These were measured using whole blood flow cytometry. Measurement after incubation with agonists such as ADP was also performed in order to assess the platelet responsiveness to stimuli.

Ultegra Rapid Platelet Function Assay (RPFA).

Methods:

Venepuncture:

Venous blood was collected into vacutainers by clean venepuncture with 19G butterfly and adaptor, using tourniquet to locate the vein only. The first 5 mL of blood was used for full blood count, and subsequent samples collected in order for the platelet tests and others.

Points of Care Platelet Aggregation Tests:

Platelet aggregation was measured using the RPFA Ultegra with Verify now cartridges for Aspirin and GPIIB/IIIA (Accumetrics, San Diego, Calif.). This is a well-validated, point-of-care system which tests the ability of activated platelets in whole blood to bind fibrinogen-coated micro-beads contained within the cartridge test wells. Blood is stimulated with either thrombin-receptor activating peptide (TRAP) in the GPIIB/IIIA assay, or arachidonic acid (AA) in the Aspirin assay. Results are reported as platelet aggregation units (PAU) for the GPIIB/IIIA assay and aspirin reaction units (ARU) for the Aspirin variations is 5.8% for RPFA-Aspirin and 5.0% for RPFA-GPIIB/IIIA.

Platelet Activation:

Platelet activation status was assessed as fibrinogen binding to resting and stimulated platelets by whole blood flow cytometry (Goodhall and Appleby) as previously validated in our laboratory (e.g., Cassar K, et al 2003). Briefly, citrate-anticoagulated blood was diluted ten-fold with HEPES-Mg buffer within 10 minutes of blood sampling. Diluted blood was incubated with FITC-conjugates rabbit anti-human fibrinogen antibody (Dako Cytomation, Denmark), for 20 minutes and the reaction was stopped by dilution with cold PBS. In order to assess the responsiveness of platelets to agonist stimulation, samples were incubated for 5 min with $10^{-5}$M or $10^{-6}$M ADP (Sigma Chemical Co. Ltd UK), $10^{-5}$M 5-HT or a combination of $10^{-6}$M ADP and $10^{-5}$M 5-HT, before addition of antibodies. Samples were analysed on the Coulter EPICS-XL flow cytometer (Bechman Coulter Inc, Ca, USA). Platelets were identified and gated in a separate sample by forward and side-scatter and by positive labelling with FITC-conjugated CD61 antibody, which binds specifically to platelet glycoprotein IIIa (Dako Cytomation, Denmark). Results are expressed as percentage of platelets positive for fluorescent antibody staining for fibrinogen.

Thromboserin Assay

Plasma was prepared by centrifugation of citrate-anticoagulated blood at 2500×G for 10 minutes, within 1 hour of venepuncture, frozen and stored at −80° C. until assay. Plasma Thromboserin concentrations were determined by liquid chromatography/mass spectrometry/mass spectrometry (LC/MS/MS), i.e., liquid chromatography tandem mass spectrometry. The LC part separates the mixture into its individual components and then quantification is by using two stages of mass spectrometry, i.e., scan for the parent ion, fragment it and scan for a specific fragment. This is a very sensitive and very selective method. Fifty microlitres of plasma were precipitated by vortex mixing with 200 μl of acetonitrile containing 100 ng/ml imipramine as the internal standard and centrifuged at 10,000 rpm for five minutes. Five micro litres of the supernatant was injected onto the chromatograph. Imipramine and Thromboserin were resolved on a Nucleosil 5 μm ODS column (150×4.6 mm) with a mobile phase of 20% 0.1% triethylamine, pH 4.0 and 80% acetrontrile at a flow rate of 1 mL/min, which was split to allow 200 μL/min through the mass spectrometer. The first four minutes after injection were diverted to waste. Both compound were analysed using an electrospray source in positive ion mode and quantification performed on the SRM transition fragments m/z 337.1-m/z 292.1 for Thromboserin and m/z 281.1-m/z 86.1 for imipramine. Calibration standards and quality control samples were prepared by spiking blank plasma with known concentrations of Thromboserin and processing as described for the patent samples. The detector response was linear up to 1000 ng/ml with a lower limit of quantification of 1 ng/ml.

Skin Bleeding Time:

Skin bleeding time was performed, contra-laterally from venepuncture. A suitable area of forearm was shaved if necessary and cleaned with alcohol swab. A sphygmomanometer cuff was inflated on the upper arm to 40 mmHg. One incision was made with Surgicutt bleeding device (Elitech, Hertfordshire), and a stopwatch was started. Filter paper (Whatman No. 1) was applied t the droplet at 30-second intervals, avoiding touching the skin, until bleeding stopped. The bleeding time was recorded to the nearest 30 seconds.

Clinical symptoms and signs were also recorded. The other observations were: routine full blood count by Clinical Haematology Laboratory, ARI, and U&Es, creatinine, Liver Function tests and blood glucose by Clinical Biochemistry Laboratory, ARI.

Rationale for Platelet Function Assays

Whole blood flow cytometry is the 'gold standard' for investigating in vivo platelet activation. Unlike aggregometry it avoids artifactual platelet activation. However, flow cytometry does require expertise, time and expensive equipment. The Ultegra-RPFA is a point-of-care system that provides a quantitative measure of platelet function as reflected by the ability to agglutinate fibrinogen-coated beads. Results correlate well with those from conventional aggregometry, but the Ultegra method has the advantage of requiring a smaller blood sample, minimising artefactual activation and giving rapid results (Steinhubl S, Talley D J, Braden G A, et al. Point-of-care measured platelet inhibition correlates with a reduced risk of an adverse cardiac event after percutaneous coronary intervention. Results of the GOLD (AU-Assessing Ultegra) Multicenter Study. Circulation. 2001; 103: 2572-2578; Wheeler, Braden and Steinhubl, American Heart Journal. 143(4): 602-611, April 2002).

Table 1 shows the bleeding times for the first 13 patients for whom data was obtained.

| Control | Course 1 | Washout | Course 2 | Washout |
| --- | --- | --- | --- | --- |
| 360 | 210 | 300 | 210 | 180 |
| 540 | 360 | 420 | 330 | 390 |
| 360 | 330 | 330 | 390 | 330 |
| 360 | 300 | 240 | 270 | 300 |
| 360 | 540 | 360 | 360 | 300 |

-continued

| Control | Course 1 | Washout | Course 2 | Washout |
|---------|----------|---------|----------|---------|
| 210 | 210 | 210 | 210 | 150 |
| 360 | 240 | 360 | 240 | 210 |
| 270 | 270 | 270 | 210 | 270 |
| 150 | 270 | 270 | 270 | 210 |
| 270 | 390 | 240 | 300 | 270 |
| 270 | 240 | 270 | 210 | 240 |
| 300 | 180 | 150 | 270 | 270 |
| 210 | 210 | 300 | 240 | 270 |

The numbers refer to seconds of bleeding after a standardised skin prick.

Course 1 was randomised drug versus placebo and Course 2 was the opposite for each patient (cross-over)—it was a "double blind randomised cross-over trial".

The lack of differences between the cross-over group show that there is no significant rise in bleeding time in any patient during either course.

The full statistical analysis of the test data obtained from the 48 patients is displayed below.

| Variable | Probability of no Difference | test used |
|----------|------------------------------|-----------|
| Bleeding time | NS | paired t test |
| Platelet count | 0.0416 | Wilcoxon |
| Platelets, excluding 4 patients | | |
| With abnormal count | 0.0214 | WIlcoxon |
| Platelet count over 6 weeks | 0.0233 | Repeated measures ANOVA |
| Platelet function:- | | |
| Ultegra ASA | NS | paired t test |
| Iltegra Iib/IIIa | NS | paired t test |
| Flow cytometry, resting fibrinogen | NS | paired t test |
| Flow cytometry + 10 μM ADP | NS | Wilcoxon |
| Flow cytometry + 1 μM ADP | NS | Wilcoxon |
| Flow cytometry + 1 μM ADP + 10 μM 5HT | NS | paired t test |
| Biochemistry:- | | |
| Bilirubin | NS | paired t test |
| Alkaline phosphatase | 0.0034 | paired t test |
| In patients with abnormal values | NS | Wilcoxon |
| Alanine amino transferase | 0.0021 | Wilcoxon |
| In patients with abnormal values | NS | Wilcoxon |
| Gamma GT | 0.0216 | Wilcoxon |
| In patients with abnormal values | 0.0266 | Wilcoxon |
| Glucose | NS | paired t test |
| Urea | NS | paired t test |
| Creatinine | NS | paired t test |
| Sodium | NS | Wilcoxon |
| Potassium | NS | paired t test |
| Chloride | NS | Wilcoxon |
| Haematology:- | | |
| Haemoglobin | NS | Wilcoxon |
| RBC | NS | paired t test |
| WBC | NS | Wilcoxon |
| Cardiology:- | | |
| QTc | NS | paired t test |
| Heart rate | NS | paired t test |

The effect on platelet count is more clearly shown by repeated measured analysis of variance in the patients given Thromboserin first (FIG. 1).

REFERENCES

[2.] Huo, Y., Ley, F. Platelet activation in atherosclerosis. *Trends in Cardiovas. Dis.,* 2004, 14, 18-22.

[16.] Antman, E. A. The re-emergence of anticoagulation in coronary disease. *Eur. H. J.* 2004, 6 (Suppl B), B2-B8.

[17.] Wallentin, L. Oral direct thrombin inhibition for anticoagulation in coronary artery disease—focus on the ESTEEM trial. *Eur. H. J.,* 2004, 6 (Suppl B), B9-B14.

[82.] Menys, V. C., Smith, C. C. T., Lewins, P., Farmer, R. D. T., Noble, M. I. M. Platelet 5-hydroxytryptamine is decreased in a preliminary group of depressed patients receiving the 5-hydroxytryptamine re-uptake inhibiting drug fluoxetine. *Clin. Sci.,* 1996, 91, 87-92.

[94.] McAuliffe, S. J. G., Snow, H. M., Smith, C. C. T., Noble, M. I. M. Interaction between effects of 5-hydroxytryptamine and adrenaline on the growth of platelet thrombi in the coronary artery of the anaesthetised dog. *Br. J. Pharmacol.,* 1993, 109, 405-410.

[95.] Belcher, P. R., Drake-Holland, A. J., Hynd, J., Noble, M. I. M. Dispersion of coronary artery thrombi by antagonism of platelet serotonin receptor in the dog. *Cardiovasc. Res.,* 1992, 26, 292-296.

[97.] Ton, S., Noble, M. I. M., Folts, J. D. Inhibition of acute platelet thrombosis formation in stenosed canine coronary arteries by the specific serotonin 5HT$_2$ receptor antagonist ritanserin. *Cardiovasc. Res.,* 1990, 24, 465-470.

[139.] Heart Advice I've been taking aspirin for 25 years, and clopidogrel for several years. I've had a number of heart attacks. You reported recently on people who can't benefit from aspirin, and I think I may be one of them. What should I do? *Heart Advisor (United States,)* 2004, 7, 8.

[142.] Cerrito, F., Lazzaro, M. P., Gaudio, E., Arminio, P., Aloisi, G. 5HT$_2$-receptors and serotonin release: their role in human platelet aggregation. *Life Sci.,* 1993, 53, 209-215.

[143.] Noble, M. I. M., Drake-Holland, A. J. The involvement of serotonin in the formation of thrombi at critical coronary artery stenoses in humans. *Co. Art. Dis.,* 1990, 1, 675-679.

[144.] Noble, M. I. M., Drake-Holland, A. J. Evidence for a role of serotonin in initiation of coronary arterial thrombosis in dog and man. *Clin. Physiol. Biochem.,* 1990, 8(suppl 3), 50-55.

[145.] Noble, M. I. M., Drake-Holland, A. J. The possible role of serotonin 5HT$_2$ receptor antagonism in cardioprotection. *Neth. J. Med.,* 1992, 41, 183-189.

[146.] Noble, M. I. M., Drake-Holland, A. J. Mini-review: The role of serotonin 5HT$_2$ receptor antagonism in the control of coronary artery disease. *Q. J. Med.,* 1994, 87, 11-16.

[147.] Belcher, P. R., Drake-Holland, A. J., Noble, M. I. M. Antagonism of the platelet 5HT$_2$ receptor in the presence of thrombolysis. *Internat. J. Cardiol.,* 1994, 43, 11-20.

[148.] Vikenes, K., Farstad, M., Nordrehaug, J. E. Serotonin is associated with coronary artery disease and cardiac events. *Circulation,* 1999, 100, 483-489.

[149.] Yamada, S., Akita, H., Kanazawa, K., Ishida, T., Hirata, K., Ito, K., Kawashima, S., Yokoyama, M. T102C polymorphism of the serotonin (5HT) $_{2A}$ receptor gene in patients with non-fatal acute myocardial infarction. *Atherosclerosis,* 2000, 150, 143-148.

[150.] Ozdener, F., Gulbas, Z., Erol, K., Ozdemir, V. 5-Hydrohytryptamine-2A receptor gene (HTR 2A) candidate polymorphism (T 102 C): role for human platelet function under pharmacological challenge ex vivo. *Meth. Find. Expl. Clin. Pharmacol.,* 2005, 27, 395-400.

[151.] Drake-Holland, A. J. Modification of coronary artery disease using antithrombotic therapy? *J. Cardiovasc. Risk,* 1995, 2, 229-233.

[152.] Jackson, S. P., Schoenwaelder, S. M., Goncalves, I., Nesbitt, W. S., Yap, C. L., Wright, C. E., Kenche, V., Anderson, K. E., Dopheide, S. M., Yuan, Y., Sturgeon, S. A., Prabaharan, H., Thompson, P. E., Smith, G., Shepherd, P. R., Daniella, N., Kulkarni, S., Abbott, B., Saylik, D., Jones, C., Lu, L., Giuliano, S., Hughan, S. C., Angus, J. A., Robertson, A. D., Salem, H. PI 3-kinase p110β: a new target for antithrombotic therapy. *Nature Medicine*, 2005, 10, 1038/nm1232.

[153.] Cohen, H. W., Gibson, G., Alderman, M. H. Excess risk of myocardial infarction in patients treated with antidepressant medication: association with use of tricyclic agents. *Am. J. Med.*, 2000, 1082-1088.

[154.] Bakish, D., Cavazzoni, P., Chudzik, J., Ravindran, A., Hrdina, P. D. Effects of selective serotonin reuptake inhibitors on platelet serotonin parameters in major depressive disorder. *Biol. Psychiat.*, 1997, 41, 184-190.

[155.] Glassman, A. H., O'Connor, C. M., Califf, R. M., Swedberg, K., Schwartz, P., Bigger, J. T., Jr., Krishnan, K. R., van Zyl, L. T., Swenson, J. R., Finkel, M. S., Landau, C., Shapiro, P. A., Pepine, C. J., Mardekian, J., Harrison, W. M., Barton, D., McIvor, M., SADHEART Investigators. Sertraline Antidepressant Heart Attack Randomised Trial (SADHEART) Group: Serotonin Uptake inhibitors modulate intracellular $Ca^{2+}$ mobilization in platelets. *Eur. J Pharmacol.*, 1995, 288, 373-377.

[156.] Glassman, A. H., O'Connor, C. M., Califf, R. M., Swedberg, K., Schwartz, P., Bigger, J. T. J., Krishnan, K. R., van Zyl, L. T., Swenson, J. R., Finkel, M. S., Landau, C., Shapiro, P. A. Sertraline treatment of major depression in patients with acute myocardial infarction or unstable angina. *J.A.M.A.*, 2002, 288, 701-709.

[157.] Helmeste, D. M., Tang, S. W., Reist, C., Vu, R. Serotonin uptake inbibitors modulate intracellular $Ca^{2+}$ mobilization in platelets. *Eur. J. Pharmacol.*, 1995, 288, 373-377.

[158.] Markovitz, J. H., Shuster, J. L., Chitwood, W. S., May, R. S., Tolbert, L. C. Platelet activation in depression and effects of sertraline treatment: an open-label study. *Am. J. Psychiat.*, 2000, 157, 1006-1008.

[159.] Meier, C. R., Schlienger, R. G., Jick, H. Use of selective serotonin reuptake inhibitors and risk of developing first-time acute myocardial infarction. *B. J. Clin Pharmacol.*, 2001, 52, 179-184.

[160.] Serebruany, V., Glassman, A., Malinin, A., Sane, D., Finkel, M., Krishnan, R., Atar, D., Lekht, A., O'Connor, C. Enhanced platelet/endothelial activation in depressed patients with acute coronary syndromes: evidence from recent clinical trials. *Blood Coag. Fibrinol.*, 2003, 14, 563-567.

[161.] Rosel, P., Arranz, B., Vallejo, J., Alvarez, P., Menchon, J., Palencia, T., Navarro, M. Altered $^{(3H)}$imiprimine and 5-HT but not $^{(3H)}$paroxetine binding sites in platelets from depressed patients. *J. Aff. Dis.*, 1999, 52, 225-233.

[162.] Pandey, G., Pandey, S., Janicek, P., Marks, R., Davis, J. Platelet serotonin-2 receptor binding sites in depression and suicide. *Biol. Psychiat.*, 1990, 28, 215-222.

[163.] Eckert, A., Gann, H., Riemann, D., Aldenhoff, J., Muller, W. Elevated intracellular calcium levels after $5-HT_2$ receptor stimulation in platelets of depressed patients. *Biol. Psychiat.*, 1993, 34, 565-568.

[166.] Ashton, J. H., Benedict, C. R., Fitzgerald, C., Raheja, S., Taylor, A., Campbell, W. B., Buja, L. M., Willerson, J. T. Serotonin as a mediator of cyclic flow variations in stenosed canine coronary arteries. *Circulation*, 1986, 73, 572-578.

[167.] Ashton, J. H., Golino, P., McNatt, J. M., Buja, L. M., Willerson, J. T. Serotonin $S_2$ and thromboxane $A_2$-prostaglandin $H_2$ receptor blockade provide protection against epinephrine-induced cyclic flow variations in severely narrowed canine coronary arteries. *J. Am Coll. Cardiol.*, 1989, 13, 755-63.

[168.] Grover, G. J., Parham C. S, Youssef S, M. I., O. Protective effect of the serotonin receptor antagonist cinanserin in two canine models of pacing-induced myocardial ischaemia. *Pharmacol.*, 1995, 50, 286-297.

The invention claimed is:

1. A method comprising administering pre-operatively, during a surgical operation, or post-operatively an amount ranging from about 20 mg to about 100 mg daily of a $5-HT_{2A}$ receptor antagonist comprising thromboserin or a pharmaceutically acceptable salt thereof to treat or prevent thrombosis in a human or animal patient characterized in that administration results in a statistically insignificant variation in bleeding time during surgery.

2. The method according to claim 1 wherein the thrombosis is coronary arterial thrombosis.

3. The method according to claim 1 wherein the $5-HT_{2A}$ receptor antagonist is given pre-operatively to patients at high risk of cardiovascular complications following surgery.

4. The method according to claim 1 wherein the pharmaceutically acceptable salt of thromboserin is the hydrogen chloride salt.

5. The method according to claim 1 wherein the patient is elderly.

6. The method according to claim 1 wherein the patient suffers or has or has suffered with cerebrovascular accident, myocardial infarction, thoracic syndrome, intermittent claudication, coronary heart disease, atherosclerosis or other atherosclerotic disease.

7. The method according to claim 1 wherein the patient is unable to take known anti-thrombotic therapies because of bleeding risks.

8. The method according to claim 1 wherein the treatment is prophylactic.

9. The method according to claim 1 wherein the surgical operation is a coronary artery bypass.

10. The method according to claim 1 wherein the surgical operation is a coronary angioplasty with a stent insertion.

11. The method according to claim 1 wherein the surgical operation is a peripheral angioplasty.

12. The method according to claim 1 wherein the patient possesses a source of bleeding.

13. The method according to claim 12 wherein the source of bleeding is a cerebral lesion.

14. The method according to claim 12 wherein the source of bleeding is the gastro-intestinal or urinary tract.

15. The method of claim 1 wherein the patient is undergoing atherothrombotic therapy.

16. Thee method of claim 15 wherein the atherothrombotic therapy comprises administration of an effective amount of one or more compounds selected from the group consisting of aspirin, statins, β-blockers, ACE inhibitors, Angio II receptor antagonists, diuretics, nicorandil, nitrates diabetes drugs and arthritis drugs.

17. The method of claim 2 whereln the patient is elderly, the patient is undergoing antithrombotic therapy, the patient possesses a source of bleeding, or combinations thereof.

18. The method of claim 3 wherein the patient is elderly, the patient is undergoing antithrombotic therapy, the patient possesses a source of bleeding, or combinations thereof.

19. The method of claim 6 wherein the patient is elderly, the patient is undergoing antithrombotic therapy, the patient possesses a source of bleeding, or combinations thereof.

20. A. method comprising administering pre-operatively, during a surgical operation, or post-operatively from about 10 mg to about 30 mg two to three times daily of a 5-HT$_{2A}$ receptor antagonist consisting essentially of thromboserin or a pharmaceutically acceptable salt thereof to treat or prevent thrombosis in a human or animal patient characterized in that administration results in a statistically insignificant variation in bleeding time during surgery.

21. A method comprising administering pre-operatively, during a surgical operation, or post-operatively from about 10 mg to about 20 mg two to three times daily of a 5-HT$_{2A}$ receptor antagonist consisting essentially of tbromboserin or a pharmaceutically acceptable salt thereof to treat or prevent thrombosis in a human or animal patient characterised in that the patient is undergoing atherothrombotic therapy and that administration results in a statistically insignificant variation in bleeding time during surgery.

22. A method comprising administering perioperatively from about 10mg to about 20 mg two to three times daily of a 5-HT$_{2A}$ receptor antagonist consisting essentially of thromboserin or a pharmaceutically acceptable salt thereof to treat or prevent thrombosis in a human or animal patient characterised in that the patient is at risk of developing arterial thrombosis and that administration results in a statistically insignificant variation in bleeding time during surgery.

23. The method of claim 1 wherein the amount ranges from 50 mg to 100 mg.

24. The method of claim 1 wherein a statistical insignificance is determined using a paired t-test having a p-value greater than 0.05.

25. A method comprising administering pre-operatively, during a surgical operation, or post-operatively an amount ranging from about 30 mg to about 100 mg of a 5-Ht$_{2A}$ receptor antagonist comprising thromboserin or a pharmaceutically acceptable salt thereof daily to treat or prevent thrombosis in a human or animal patient at risk of bleeding characterized in that administration results in a statistically insignificant variation in bleeding time during surgery.

\* \* \* \* \*